(12) United States Patent
Ladebeck

(10) Patent No.: US 8,768,432 B2
(45) Date of Patent: Jul. 1, 2014

(54) METHOD FOR ABSORPTION CORRECTION OF PET DATA AND MR-PET SYSTEM

(75) Inventor: Ralf Ladebeck, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 305 days.

(21) Appl. No.: 12/822,289

(22) Filed: Jun. 24, 2010

(65) Prior Publication Data

US 2010/0331665 A1  Dec. 30, 2010

(30) Foreign Application Priority Data

Jun. 26, 2009  (DE) .......................... 10 2009 030 714

(51) Int. Cl.
| | | |
|---|---|---|
| A61B 5/055 | (2006.01) | |
| A61B 6/03 | (2006.01) | |
| A61B 6/00 | (2006.01) | |
| A61B 5/107 | (2006.01) | |
| G01R 33/48 | (2006.01) | |
| G06F 19/00 | (2011.01) | |

(52) U.S. Cl.
CPC ............... *A61B 6/032* (2013.01); *A61B 6/5247* (2013.01); *A61B 6/4417* (2013.01); *A61B 6/037* (2013.01); *A61B 5/1077* (2013.01); *G01R 33/481* (2013.01); *G06F 19/321* (2013.01)
USPC ........... 600/411; 600/425; 324/309; 382/128; 382/131

(58) Field of Classification Search
CPC ...... A61B 6/032; A61B 6/037; A61B 6/5247; A61B 6/4417; A61B 5/1077; G01R 33/481; G06F 19/321
USPC .................. 600/407, 411, 426, 427; 382/131; 250/341.1
See application file for complete search history.

(56) References Cited

U.S. PATENT DOCUMENTS

| | | | | |
|---|---|---|---|---|
| 7,327,138 | B2 * | 2/2008 | Krieg et al. .................... | 324/307 |
| 7,925,326 | B2 * | 4/2011 | Siegel et al. ................... | 600/414 |
| 8,005,285 | B2 * | 8/2011 | Kunze ............................. | 382/131 |
| 2005/0096537 | A1 * | 5/2005 | Parel et al. ..................... | 600/427 |
| 2005/0129295 | A1 * | 6/2005 | Shanmugam et al. ........ | 382/131 |
| 2006/0270917 | A1 * | 11/2006 | Pfeiler .......................... | 600/300 |
| 2007/0019850 | A1 * | 1/2007 | Knoplioch et al. ............ | 382/131 |
| 2007/0114418 | A1 * | 5/2007 | Mueller et al. ............. | 250/341.1 |
| 2007/0131858 | A1 * | 6/2007 | Wollenweber et al. ..... | 250/252.1 |
| 2007/0296957 | A1 * | 12/2007 | Fitzgerald et al. .............. | 356/51 |
| 2008/0262344 | A1 * | 10/2008 | Brummett ...................... | 600/426 |
| 2009/0041318 | A1 |  2/2009 | Feiweier et al. | |
| 2009/0206263 | A1 * | 8/2009 | Rahman ...................... | 250/341.1 |
| 2011/0251480 | A1 * | 10/2011 | Graves et al. ................. | 600/411 |
| 2012/0095322 | A1 * | 4/2012 | Tsekos et al. ................. | 600/411 |

FOREIGN PATENT DOCUMENTS

| | | |
|---|---|---|
| DE | 102007044860 A1 | 12/2008 |
| DE | 102007034953 A1 | 2/2009 |

* cited by examiner

*Primary Examiner* — Baisakhi Roy
(74) *Attorney, Agent, or Firm* — Harness, Dickey & Pierce, P.L.C.

(57) ABSTRACT

An apparatus is disclosed for combined magnetic resonance tomography and positron emission tomography imaging which is designed for recording PET image data of a person under examination from an examination area. In at least one embodiment, the apparatus includes a scanning unit, embodied to scan a prespecified area of the person under examination and based on the scanning, to determine a contour of the person under examination for the prespecified area; and a processing unit, embodied, based on the contour determined, to carry out an absorption correction of PET data which has been recorded from the prespecified area of the person under examination. A method is also disclosed.

30 Claims, 3 Drawing Sheets

METHOD FOR ABSORPTION CORRECTION OF PET DATA AND MR-PET SYSTEM

PRIORITY STATEMENT

The present application hereby claims priority under 35 U.S.C. §119 on German patent application number DE 10 2009 030 714.1 filed Jun. 26, 2009, the entire contents of which are hereby incorporated herein by reference.

FIELD

At least one embodiment of the present invention generally relates to a device for combining Magnetic Resonance (MR) tomography and Positron Emission Tomography (PET) imaging and/or a method for absorption correction of PET data.

BACKGROUND

Positron Emission Tomography (PET) is a widely-used method of functional imaging. During an examination a weak radioactive substance, of which the distribution in the organism is made visible by way of PET, is administered to a person being examined. This enables biochemical and physiological functions of the organism to be mapped. In such cases molecules which are marked with a radio nuclide which emits positrons are used as radiopharmaceuticals. The high-energy photons, which are emitted at an angle of 180° to each other, produced in the body of the person under examination during the annihilation of the positron with an electron are detected by a plurality of detectors arranged in a ring around the person under examination. Only coincident events which have been detected with two opposite detectors are evaluated in each case.

From the registered coincident decay events deductions are made about the spatial distribution of the radio pharmaceutical within the body and a series of image slices are computed. The image can be reconstructed in such cases with a filtered back projection or an iteration method, with the spatial resolution usually lagging behind the resolution of conventional computer tomography (CT) or magnetic resonance tomography (MRT).

On their passage through material the photons produced during the annihilation can be absorbed, with the absorption probability depending on the path length through the material and the corresponding absorption coefficient of the material. Accordingly in PET a correction of the signals in relation to the attenuation by components which are located in the beam path is necessary. In particular such a correction has to be undertaken if a quantitative analysis of the data is to be carried out for example for quantifying accumulations of the marked substance (i.e. the radiopharmaceutical) in areas of the person under examination. In image reconstruction too not taking account of the absorption of the radiation leads to the occurrence of artifacts, since the measured activity distribution without absorption correction does not match the actual distribution. The correction of the attenuation of the radiation requires the knowledge of the location of the attenuating structures which are taken into account during reconstruction of PET image data by means of an attenuation correction map (µ-map).

An attenuation correction map can be determined with a combined PET/CT system. The correction maps can be calculated in such cases from the Hounsfield values of the CT data. This method is made possible by the x-ray radiation of the CT undergoing a similar attenuation on its passage through the person under examination to the high-energy photons during the recording of the PET signals. Furthermore such systems enable the high local resolution of CT to be combined with the functional imaging of PET.

CT devices have the disadvantage however that damaging x-rays are used and that only a low soft tissue contrast can be achieved without contrast media. However a high soft tissue contrast is desirable, especially in functional imaging of the brain.

A high local resolution with simultaneous high soft tissue contrast as well as a functional imaging can be achieved with a combination of PET and magnetic resonance tomography (MRT). Such a system simultaneously enables high resolution images of the brain structure to be delivered and functional activities in the brain to the mapped. MRT allows different types of tissue to be differentiated, while PET makes physiological and biochemical activities visible. However it is problematic to derive coefficients of attenuation for the high-energy photons of the PET imaging from the MRT image data, i.e. to determine the attenuation correction map. Furthermore the recording of MRT image data demands a significantly longer acquisition time than the creation of computer tomographies.

To take into account the attenuation of the emitted photons through the body any deviations of the MRT imaging from the true geometry are also disruptive. In this case areas of the body which, although they lie in the PET beam path, are not mapped or not mapped at the correct position pose a particular problem. In particular because of the high ratio of the attenuation coefficient (µ value) of human tissue to air it is desirable for a correct attenuation correction to determine the spatial transition from air to tissue as exactly as possible.

SUMMARY

In at least one embodiment of the present invention, an improved absorption correction of PET data is provided in an MR-PET system.

In accordance with the first aspect of at least one embodiment of the present invention an apparatus for combined magnetic resonance tomography and positron emission tomography (PET) imaging is provided which is equipped for recording PET image data of a person under examination from an area under examination. The apparatus includes an additional scanning unit which is equipped to scan a prespecified area of the person under examination and, based on the scanning, to determine a contour of the person under examination for the prespecified area, as well as a processing unit which is equipped, on the basis of the contour determined, to carry out an absorption correction of PET data which has been recorded from the prespecified area of the person under examination.

By way of the additional scanning unit the contour or surface of the person under examination can be detected so that the position of the body parts of the person under examination is known and can be used for absorption correction of PET signals or PET image data. By way of the scanning unit the contour of the person under examination can be determined significantly more quickly and with a larger field of view than with an imaging MRT measurement and an improved absorption correction is made possible.

In one embodiment, the additional scanning unit can be arranged in the direction in which the person under examination is pushed into the examination area, with the scanning unit having a scanning area which is different from the examination area of the apparatus. In the examination the person under examination is thus for example initially moved through the scanning area of the scanning unit and subsequently through the examination area of the apparatus, i.e. of the MR-PET system. The scanning unit can thus be integrated more easily into the MR-PET system and existing MR-PET systems can be upgraded in a simple manner. In particular it is advantageous for the scanning area to have a larger field of view than the examination area of the MRT imaging.

The scanning unit is equipped for example for scanning the surface of a slice of the person under examination. The apparatus can have a patient table for moving the person under examination through the examination area, with the scanning unit scanning the prespecified area of the person under examination in slices during a typically step-by step method of movement of the patient table. Consequently the surface of the person under examination in the prespecified area can be determined in three dimensions by placing the scanned slices next to each other, with the prespecified area also able to comprise the whole person under examination.

The apparatus can be embodied for simultaneously executing a PET measurement and scanning the person under examination by way of the scanning unit. The recording of the PET data or signals and the determination of the contour of the person under examination by means of scanning can therefore take place during one measurement pass. It is also possible to simultaneously carry out an MRT measurement during the scanning of the person under examination with the scanning unit. It is likewise possible to record both PET and MRT data in one measurement run and also to carry out the scanning of the person under examination. This enables locally high-resolution image data with functional information from the PET image data to be obtained, which has been absorption-corrected based on the scanning carried out simultaneously.

The processing unit can be embodied, based on the contour determined, to create an attenuation correction map (μ-map) of the scanned area. The absorption correction of the PET data can be undertaken on the basis of the attenuation correction map. A rapid determination of the attenuation correction map is thus possible with the aid of the scanning unit which approximately specifies the spatial distribution of the attenuation coefficient μ for the attenuation of the high-energy protons occurring during the positron annihilation.

The processing unit can for example be designed so that areas which are lying within the contour determined will be assigned a constant prespecified attenuation coefficient μ. The contour determined is for example the surface of the person under examination or an area of the person under examination, so that the constant attenuation coefficient, such as a previously determined attenuation coefficient for water or tissue for example, can be assigned to the inside of the person under examination. Since the variation of the attenuation coefficient from the surrounding air to the inside of the body is significantly greater than the variation within the body of the person under examination, an approximated attenuation correction map can thus be obtained in a simple manner.

The processing unit can also be designed to create the attenuation correction map taking into account information from MRT image data which was recorded by way of the apparatus during MRT imaging of the prespecified area of person under examination. Information obtained from the MRT image data can for example include the position of bones and/or of the lungs of the person under examination with these are then able to be taken into account during creation of the attenuation correction map for example in the form of prespecified attenuation coefficients for the different structures. The accuracy of the attenuation correction map can thus be improved and an improved absorption correction of the PET data can be undertaken.

In accordance with one embodiment the additional scanning unit comprises a terahertz (THz) scanner which detects terahertz radiation emitted from the body of the person under examination or reflected or scattered on the latter. Terahertz radiation typically lies within a frequency range of 100 GHz to 30 THz or in a wavelength range from 3000 μm to 10 μm. By scanning the person under examination by way of the terahertz scanner the surface of the person under examination can be determined quickly and without harmful radiation. It is also advantageous that the terahertz radiation can penetrate many materials, such as plastics or the clothing of the person under examination for example, so that a precise determination of the contours or of the surface of the person under examination is made possible. The patient table with which the person under examination is moved through the examination area of the apparatus can also be embodied so that terahertz radiation penetrates through it.

The terahertz scanner can especially be embodied so that, by emitting electromagnetic terahertz radiation and detection of terahertz radiation reflected at the person under examination, it detects the contour of the person under examination in a scanning area. The terahertz scanner can thus not only detect terahertz radiation emitted passively from the body of the person under examination, but can also actively scan the body of the person under examination by means of a terahertz radiation source. This can for example be done using a fine microwave beam, with the scanning unit also able to feature a number of radiation sources.

In accordance with a further embodiment, the additional scanning unit comprises an x-ray scanner which is designed to detect the contour of the person under examination in a scanning area by irradiating x-rays and detection of the x-rays scattered back at the person under examination. An x-ray scanner based on backscattering has the particular advantage that a weak high-energy x-ray source can be used so that the person under examination is subjected to a lower radiation dose than with conventional CT systems. The x-rays likewise penetrate the clothes of the person under examination so that the surface of the person under examination can be precisely mapped and determined by way of the scanning unit.

With the apparatus previously described a precise determination of the surface of the person under examination is thus made possible with a short measurement duration so that movement artifacts from movements of the person under examination are reduced and the surface determination is thereby improved. The scanning unit can also have a significantly larger field of view than the recording unit for MRT imaging so that an attenuation correction map can also be created for the areas of the person under examination which, although they lie within the path of the PET beam, will not be mapped however by the MRT imaging. This makes an improved absorption correction of recorded PET data possible and thereby a spatially more accurate functional mapping which is suitable for quantification.

In accordance with a further aspect of at least one embodiment of the present invention a method for absorption correction of PET data is provided, with the method being carried out with an apparatus for combined magnetic resonance tomography (MRT) and positron emission tomography (PET) imaging which is embodied for recording PET data of a person under examination from an examination area and which has an additional scanning unit. The method includes the scanning of a prespecified area of the person under examination with the scanning unit, the determination of the contour of the person under examination in the scanned area based on the scanning and the execution of an absorption correction of PET data which has been recorded from the prespecified area of the person under examination on the basis of the determined contour.

Similar advantages to those described in relation to the apparatus are obtained with at least one embodiment of the inventive method. The method makes possible an improved absorption correction of recorded PET data, i.e. through a correction of PET signals or PET image data or through an absorption correction during the reconstruction of PET image data.

In accordance with an embodiment of the inventive method the scanning can be undertaken slice-by slice. For example the scanning of the person under examination can be undertaken by moving a patient table on which the person under examination is arranged through the scanning area of the scanning unit and by slice-by-slice scanning of the prespecified area by means of the scanning unit. During the scanning of the person under examination by means of the scanning unit a PET measurement can be carried out simultaneously. It is also possible to carry out an MRT measurement simultaneously. In the method, once again based on the contour determined, an attenuation correction map (μ-map) of the scanned area can be created on the basis of which the absorption correction of the PET data is undertaken. The attenuation correction map can especially be used for the reconstruction of PET image data.

Furthermore at least one embodiment of the method can comprise one or more method steps which have been described in advance with regard to the apparatus. Naturally the features of the previously described aspects and embodiments of the invention can be combined.

BRIEF DESCRIPTION OF THE DRAWINGS

Embodiments of the invention will be described in greater detail below with reference to the enclosed drawings.

DETAILED DESCRIPTION OF THE EXAMPLE EMBODIMENTS

Figure 1:
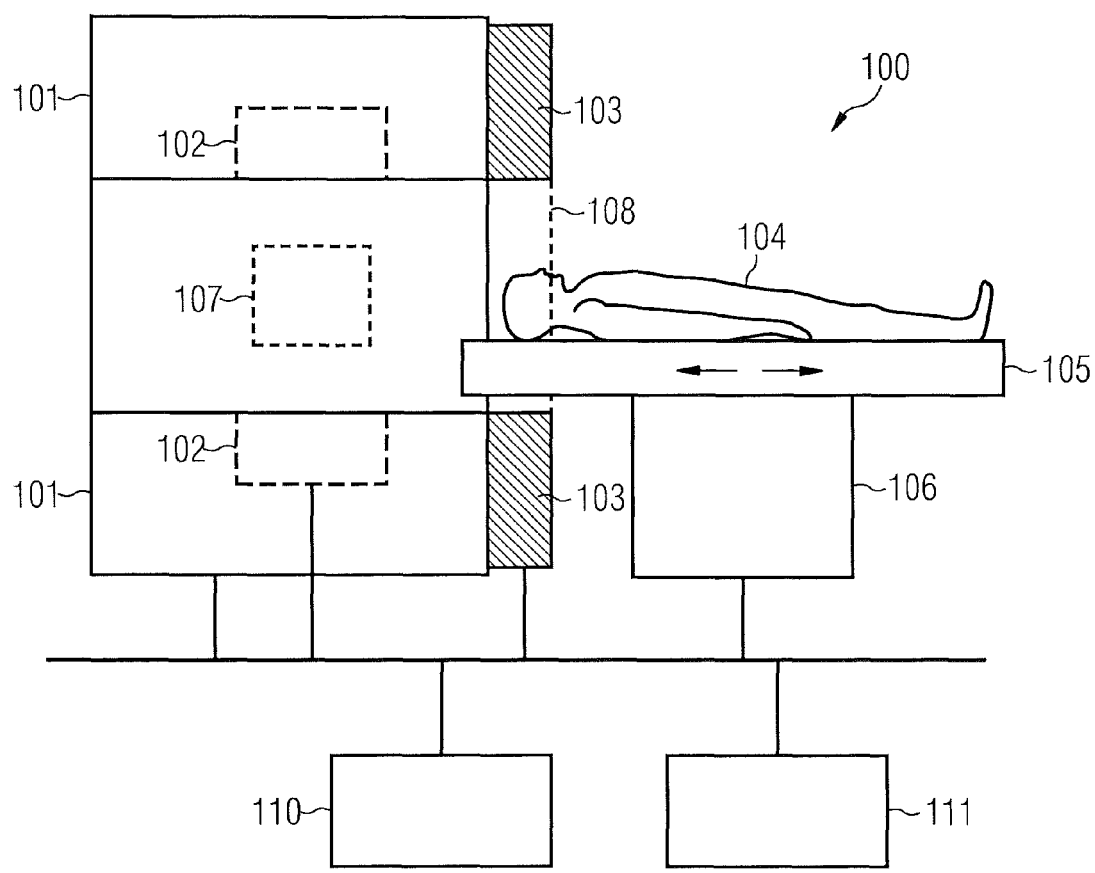
FIG. 1 shows a schematic diagram of an apparatus in accordance with an embodiment of the present invention.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows a schematic diagram of an embodiment of the inventive apparatus which is designed for combined recording of magnetic resonance tomography and positron emission tomography imaging and which is referred to below as an MR-PET system. The MR-PET system 100 features an MRT recording unit 101. This can be embodied similarly to a recording unit of a conventional magnetic resonance system. MRT recording unit 101 typically comprises a magnet for creating a polarization field $B_0$ as well as a gradient system for creating magnetic field gradients which are used for the imaging and location coding. To excite a polarization produced in the main magnetic field $B_0$ the MRT recording unit 101 also features a high-frequency coil arrangement which beams a high-frequency field into an area to be examined in order to deflect the magnetization from the position of equilibrium. The decay of the magnetization can be detected with an additional coil unit or with the high-frequency coil arrangement. Image data can subsequently be reconstructed from the recorded MR signals. Magnetic resonance signals can be recorded from an area of the $B_0$ field that is as homogeneous as possible by connecting a slice selection, phase encoding and frequency encoding gradient, from which a three-dimensional image dataset is able to be reconstructed. To record the MR signals the person under examination 104 will be moved by means of the patient table 105 into the MRT recording unit 101.

The homogenous magnetic field area from which the MR signals are recorded and for which MRT image data is subsequently reconstructed can be smaller than the area under examination 107 of the PET recording unit 102. To record PET signals a radiopharmaceutical comprising a radio nuclide which emits positrons is typically administered to the person under examination 104. The area of the person under examination 104 which is to be examined is positioned by means of the patient table 105 and the drive unit for the patient table 106 in the area under examination 107. The annihilation of a positron produced during the decay of the radio nuclide with an electron in the body of the person under examination 104 can be detected by detectors which are part of the PET recording unit 102.

The PET recording unit 102 can for example comprise a number of detectors for the high-energy photons arranged in the form of a ring around the examination area 107. PET recording unit 102 records coincidences between the two precisely opposite detectors in such cases. Based on the temporal and spatial distribution of the registered coincidence decay events, the spatial distribution of the radiopharmaceutical in the inside of the body of the person under examination 104 can be estimated. With conventional PET recording units detectors comprising a scintilla for crystal and a photomultiplier can be used. With the MR-PET system 100 however, because of the high magnetic fields in the detection of the magnetic resonance signals, semiconductor detectors such as avalanche photodiodes for example are preferably used. These avalanche photodiode detectors have a higher sensitivity for photons and can essentially be considered as the semiconductor equivalent to the photomultiplier.

Control unit 110 controls the MR-PET system 100 centrally. For example control unit 110 can control the setting up of magnetic field gradients and the irradiation of HF pulses as well as the execution of an imaging sequence to record MR signals. Furthermore it can activate the PET recording unit 102 for recording PET signals. The movement unit 106 for the patient table 105 is also activated by the control unit 110 so that the area of the person under examination 104 from which the MRT or PET image data is to be recorded is positioned in the examination area of the respective recording unit. If the area of the person under examination 104 to be imaged is larger than the field of view (FoV) of the respective recording unit, the patient table 105 can be moved in steps in order to record image data from the entire desired area consecutively. It should however be clear that the control unit 110 can also be embodied as separate control units for the respective components.

Image data from the recorded MRT or PET signals respectively is reconstructed in the processing unit 111. For example processing unit 111 reconstructs a set of spatially highly-resolved two-dimensional slice images or a three-dimensional image dataset from recorded MR signals.

In a PET measurement the high-energy photons which are generated by annihilation of the positrons emitted by a radionuclide pass through the body of the person under examination 104 so that only a week and signal is detected with the PET recording unit 102. For example a certain part of the created photons will be absorbed in the body of the person under examination 104. If this absorption remains unconsidered in the image reconstruction with the processing unit 111 this results in artifacts in the reconstructed image data.

Accordingly the activity distribution of the radiopharmaceutical determined without absorption correction does not match the actual distribution present in the person under examination 104. Because of the absorption a quantification of the nuclide administration is also not possible.

To overcome these problems processing unit 111 uses an attenuation correction by way of an attenuation correction map in the reconstruction of the PET image data. The attenuation correction map represents the spatial distribution of the attenuation coefficient $\mu$ for the photons in the relevant area.

To determine the attenuation correction map an additional scanning unit 103 is provided. Scanning unit 103 scans the person under examination 104 in a scanning area 108. This can be done slice-by-slice, with the person under examination 104 being moved step-by-step through the scanning area 108 by means of the patient table 105 and the movement unit 106. At each patient table position a slice of a specific thickness can thus be scanned. Scanning unit 103 is arranged in this case in front of the examination area 107 in the direction in which the person under examination is moved into the area. A prespecified area to be examined, e.g. the head or the thorax of the person under examination 104, can thus be scanned by way of scanning unit 103 even before the PET or MRT measurement is carried out.

The scanning can be undertaken both passively, for example by detection of radiation which is emitted by the person under examination 104, and also actively. In active scanning radiation is applied by way of scanning unit 103 and the unit also detects radiation scattered back or reflected from the person under examination 104. Based on the scanning, i.e. on the detected signal of the reflected radiation, the contour of the scanned area of the person under examination 104 is determined. For example the position of points which are located on the surface of the person under examination 104 can be detected and the surface of the person under examination can be interpolated from the points determined.

There can be an interpolation between scanned slices. If the scanning unit 103 detects a two-dimensional plane, movement of the patient table and step-by-step scanning of the person under examination allows a three-dimensional surface of the person under examination or of the area to be examined to the reconstructed. The contour can be determined in a processing unit provided separately for the scanning units 103, however it can also be carried out in the processing unit 111 of the MR-PET system 100. Processing unit 111 can in this sense also be considered as a component of the scanning unit 103.

Scanning unit 103 can be embodied for example as a terahertz scanner. In this embodiment scanning unit 103 comprises a number of terahertz detectors which are arranged in the form of a ring around scanning area 108 or are provided at prespecified positions of the scanning unit. Golay cells can be used for example as detectors for terahertz radiation. Other types of terahertz detectors can naturally also be used. The functioning of terahertz detectors is known to the person skilled in the art, so that a more detailed description is not provided at this point. Scanning units 103 can be designed as a passive scanning unit and accordingly detect terahertz radiation emitted from the body of the person under examination.

In another embodiment scanning unit 103 is an active terahertz scanner comprising one or more terahertz radiation sources. A terahertz radiation source can for example be based on forming the difference between two lasers of different wavelengths, with the laser radiation from a semiconductor element being mixed to a terahertz wave which can subsequently be emitted by a suitable antenna. Other types of terahertz source which can also be used in the scanning unit 103 are known to the person skilled in the art. The terahertz sources can for example be arranged in a ring around the scanning area 108. Other geometries are naturally also conceivable.

Terahertz radiation passes through many types of material but only has a small penetration depth in the water however. Patient table 105 can for example be designed so that terahertz radiation emitted from scanning unit 103 passes through the table. Furthermore the terahertz radiation generally passes through the clothing of the person under examination 104, so that the surface of the body of the person under examination can be scanned. The scanning of the surface can be undertaken with the aid of conventional methods which are regularly used with terahertz scanners.

Further methods are conceivable in order to determine the contour of the person under examination 104 by means of terahertz radiation. For example projection measurements can be carried out, with a terahertz source emitting radiation which is detected by detectors lying opposite it and with tissue of the person under examination lying in the beam path being absorbed/reflected and thus a contour of the person under examination being able to be detected. On the other hand it is also possible to detect terahertz radiation scattered back or reflected at the person under examination 104 and to determine the contour of the person under examination 104 from the corresponding signals. The surface of the person under examination can be sampled with a terahertz beam or a delay time measurement can be employed to determine the distance between the surface and the source/detector. As described previously, on the basis of the contours determined the surface of an area of the person under examination 104 can subsequently be interpolated.

Processing unit 111 is designed, based on the surface of the person under examination which has been determined for a prespecified area, to compute an attenuation correction map ($\mu$-map). To do this the processing unit 111 typically carries out a smoothing of the measured surface and allocates a constant attenuation coefficient $\mu$, especially a predetermined attenuation coefficient for water or tissue to areas lying within the surface determined. The attenuation correction map can thus model the transition from surrounding air to the inside of the body of the person under examination 104. Smoothing the surface determined avoids image noise being generated as a result of the attenuation correction in the reconstructed PET image data. Since the change in the attenuation coefficient on transition from air to water is significantly larger than the variation of the attenuation coefficient within the body of the person under examination 104, a good absorption correction in the reconstruction of the PET image data can already be achieved with such a $\mu$-map.

For example the $\mu$ value for air is very small (smaller than 0.0001 l/cm) in accordance with the ratio of the density of air to the density of human tissue (appr. 1:1000 l/cm). By contrast the differences between the different types of tissue of a human being are negligible. For example soft tissue has a $\mu$ value in the order of magnitude of 0.01 l/cm and bone has a $\mu$ value of 0.17 l/cm. The exact spatial determination of the transition from air to tissue which is achieved with scanning unit 103 thus makes possible an essentially artifact-free improved attenuation correction.

For further improvement of the $\mu$-map however information about the location of structures within the body of the person under examination 104 can also be used in the creation of the $\mu$-map. These structures can in particular be the lungs of the person under examination as a rule filled with air as well as the bones of the person under examination, which by comparison with other types of tissue exhibit a greater $\mu$ value contrast. For this the processing unit 111 can determine the location of bones or lung tissue from recorded MRT image data. Thus the absorption correction is further improved and a spatially more exact functional PET imaging is made possible. The MRT image data can be recorded before or after the scanning of the person under examination with the scanning unit 103.

Control unit 110 can however also be embodied so that the scanning of the person under examination by way of the scanning unit and the recording of PET and MRT data are undertaken in one measurement pass. For this movement unit 106 is activated so that the area to be examined of the person under examination is moved by first moving the patient table 105 through the scanning area 108 and subsequently through the examination area 107, with a simultaneous or time-offset recording of PET and MRT signals able to be undertaken. After reconstruction of the MRT image data the structures of interest, for example bones and lungs, will be segmented in the image data and the position of these is used in the creation of the $\mu$-map. In such cases a smoothing of the measured data can once again also be undertaken and a fixed attenuation value $\mu$ can be assigned to the inside of the lungs and to the bones.

Obtaining geometrically-exact information about the attenuating structures and thereby a quantitative PET imaging is made possible with the aid of the scanning unit 103. This was not the case with conventional MR-PET systems, since structures mapped with MRT were not shown or only shown sketchily. Scanning unit 103 can scan the surface of the person under examination significantly faster and in a significantly larger field of view than is possible with MRT imaging. In order to achieve a larger field of view in MRT imaging in the transversal direction the magnetic resonance scanner would have to be significantly enlarged. This would be associated with very high costs. Scanning unit 103 can also exclude patient-related recordings from so-called susceptibility artifacts. These types of artifact can occur in MRT imaging especially at air-tissue boundaries and cause significant distortions in the image data.

Figure 2:
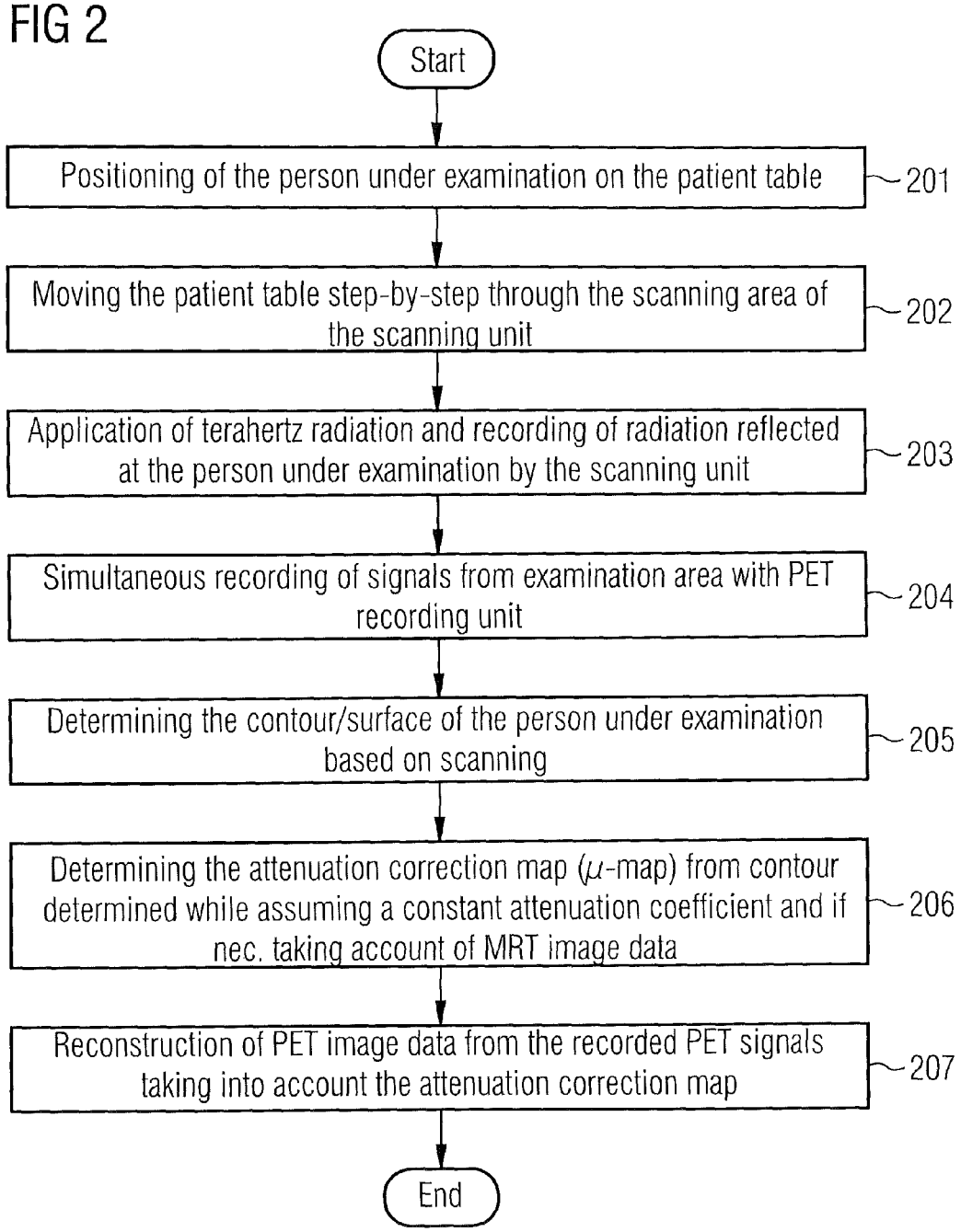
FIG. 2 shows a flow diagram of an example embodiment of the inventive method.

FIG. 2 shows a flow diagram of an embodiment of the inventive method, with the method typically able to be carried out with the MR-PET system 100 shown in FIG. 1. In step 201 the person under examination is positioned on the patient table. The patient table with the person under examination is moved in step 202 step-by-step through the scanning area of the scanning unit. In step 203 terahertz radiation is applied and the radiation reflected at the person under examination is recorded by means of the scanning unit. This scans a slice of the person under examination which is located in the scanning area of the scanning unit. Through this step-by-step movement of the patient table the entire prespecified area or even the entire person under examination can thus be scanned.

In step 204 a simultaneous reception of signals from the area under examination with the PET recording unit and/or the MRT recording unit can be undertaken. In the examination of the complete body of the person under examination, PET and MRT data can thus be recorded from an area of the person under examination while another area is being scanned with the scanning unit. This makes an efficient recording of the data possible. It also avoids the person under examination moving between the measurements so that the location of the person under examination is the same during the recording of the PET/MRT data and the scanning.

Based on the scanning, the contour or surface of the person under examination is determined in step 205. Therefore the location of the structures which attenuate the PET signal is known and can be used in step 206 to determine the attenuation correction map. This is done by assuming a constant attenuation coefficient $\mu$ and where necessary by taking account of the recorded MRT image data. In step 207 the PET image data is reconstructed from the recorded PET signals with processing unit 111, taking into account the attenuation correction map determined. Thus a functional PET imaging with improved spatial mapping is achieved.

In a further embodiment the scanning unit 103 can also be designed as an x-ray scanner (scanning unit). In such cases a scanner based on x-ray backscattering can especially be used. These types of scanners are known for example under the name "body scanner". Scanning unit 103 can in this embodiment feature one or more x-ray sources as well as a number of x-ray detectors. X-rays applied, for example because of the Compton effect, are scattered back at the surface of the person under examination 104 and the backscattered radiation is detected by means of the detectors. In this case the clothing of the person under examination is likewise essentially irradiated unhindered so that the surface of the body of the person under examination can be scanned. The slice-by-slice recording of the surface by way of the scanning unit 103 is also possible with this technique. Details of such an x-ray scanner are known to the person skilled in the art so that any further explanation is dispensed with here.

Figure 3:
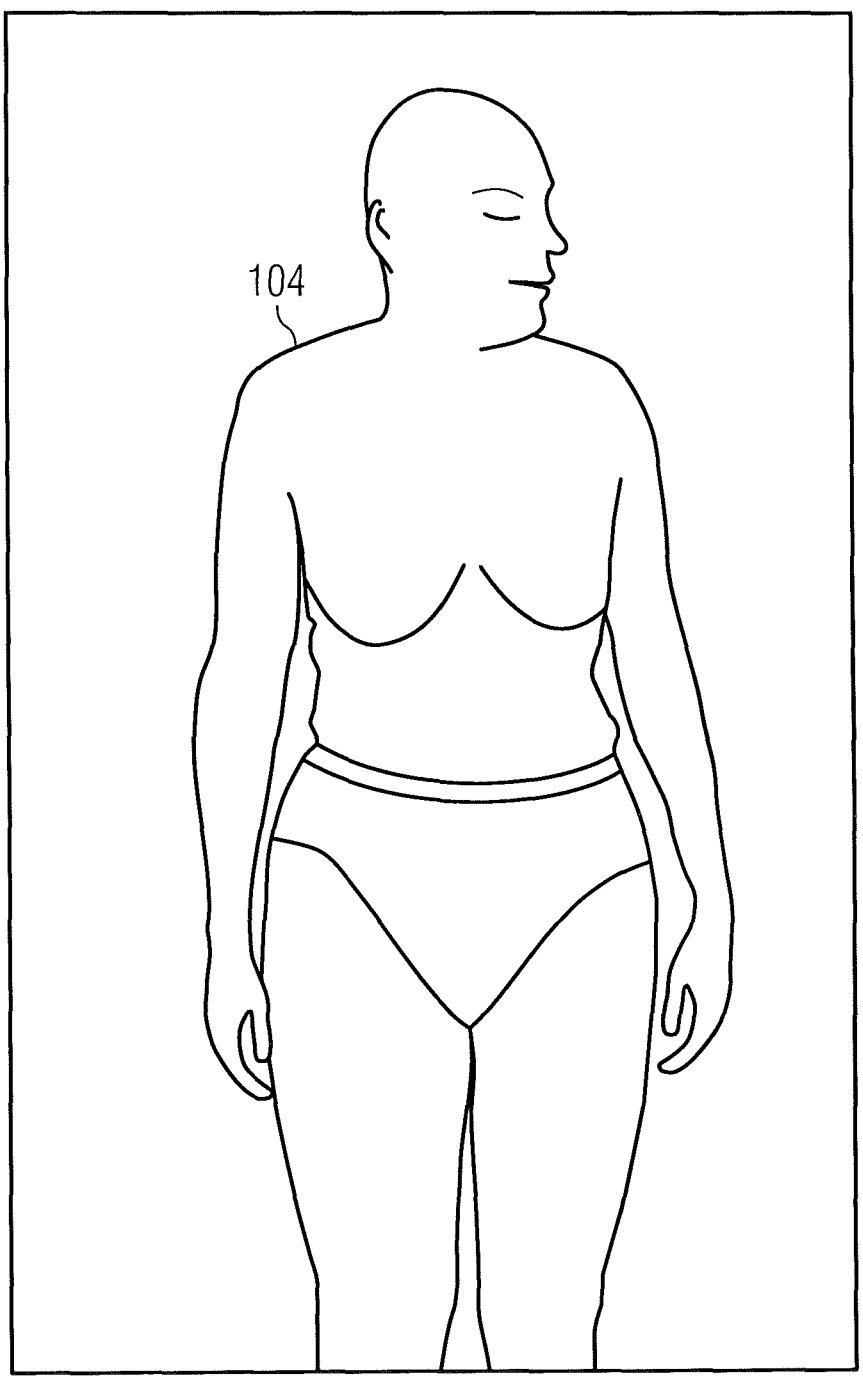
FIG. 3 shows examples of the contours of a person under examination which have been recorded with a scanning unit of an embodiment of the inventive apparatus.

FIG. 3 shows a schematic diagram of the result of scanning of a person under examination 104. By way of the scanning unit 103 scanning in three dimensions is possible so that a three-dimensional surface of the person under examination 104 can be determined. The contour of the person under examination 104 shown in FIG. 3 has been determined by means of a scanning unit 103 in the form of an x-ray scanner through detection of backscattered x-rays.

In summary at least one embodiment of the present invention makes possible the simple and precise determination of an attenuation correction map with an MR-PET system, with the attenuation correction map making possible a spatially-correct, essentially artifact-free image reconstruction of recorded PET data as well as a quantitative analysis of the latter. With the scanning unit of the MR-PET system a large field of view can be rapidly scanned. The surface of the body of the person under examination can be determined even if the person under examination is wearing clothes. By the use of terahertz or x-ray radiation, susceptibility artifacts are minimized and the rapid recording over time enables movement artifacts to be avoided. The improved spatial mapping of the PET data also makes possible a more precise superimposing or co-registration of the PET image data with recorded high-resolution MRT image data.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An apparatus for combined magnetic resonance tomography and positron emission tomography imaging, comprising:
   a structurally integrated imaging unit including,
      a single patient table,
      a magnetic resonance imaging scanner configured to record, from an examination region, MRT image data of a person under examination,
      a positron emission tomography scanner configured to record, from the examination region, PET image data of the person under examination,
      an additional scanning unit, configured to scan an area of the person under examination and based on the scanning, to determine a contour of the person under examination for the area, and
      a processor configured to,
         determine a location of structures that attenuate a PET signal based on the determined contour and the MRT image data, and
         carry out an absorption correction of the recorded PET image data from the examination region of the person under examination based on the determined location of the structures.

2. The apparatus as claimed in claim 1, wherein the additional scanning unit is arranged before the examination region in a direction in which the person under examination is moved into in the examination region, the additional scanning unit being configured to scan the area, the area differing from the examination region of the apparatus.

3. The apparatus as claimed in claim 1, wherein the additional scanning unit is configured to scan a surface of a slice of the person under examination.

4. The apparatus as claimed in claim 1, wherein the patient table is configured to move the person under examination through the examination region, the additional scanning unit being configured to scan the area of the person under examination slice-by-slice by moving the patient table.

5. The apparatus as claimed in claim 1, wherein the apparatus is configured to simultaneously carry out a PET measurement and a scan of the person under examination by way of the additional scanning unit.

6. The apparatus as claimed in claim 1, wherein the processor is configured to create an attenuation correction map of the scanned area based on the determined contour, the absorption correction of the PET data being undertaken based upon the attenuation correction map.

7. The apparatus as claimed in claim 6, wherein the processor is configured to allocate a constant attenuation coefficient to areas lying within the determined contour.

8. The apparatus as claimed in claim 7, wherein the processor is configured to create the attenuation correction map taking into account information from MRT image data recorded by way of the apparatus in an MRT imaging of the person under examination.

9. The apparatus as claimed in claim 6, wherein the processor is configured to create the attenuation correction map taking into account information from MRT image data recorded by way of the apparatus in an MRT imaging of the person under examination.

10. The apparatus as claimed in claim 1, wherein the additional scanning unit comprises a terahertz scanner configured to detect terahertz radiation emitted by the body of the person under examination or reflected from the body.

11. The apparatus as claimed in claim 10, wherein the terahertz scanner is configured to detect the contour of the person under examination in the examination region by applying electromagnetic terahertz radiation and detecting terahertz radiation reflected from the person under examination.

12. The apparatus as claimed in claim 1, wherein the additional scanning unit comprises an x-ray scanner, configured to detect the contour of the person under examination in the examination region by emitting x-rays and detecting the x-rays scattered back from the person under examination.

13. The apparatus as claimed in claim 1, wherein the patient table and the additional scanning unit are movable relative to one another, the additional scanning unit being configured to scan the area of the person under examination slice-by-slice by relative movement between the patient table and the additional scanning unit.

14. The apparatus as claimed in claim 13, wherein the patient table is configured to move the person under examination through the examination region such that the additional scanning unit is useable to scan the area of the person under examination slice-by-slice upon moving the patient table.

15. The apparatus as claimed in claim 1, wherein
   the additional scanning unit has a larger field of view than the magnetic resonance imaging scanner and the positron emission tomography scanner.

16. A method for absorption correction of PET data, the method being carried out with a structurally integrated imaging apparatus for combined magnetic resonance tomography and positron emission tomography imaging, the structurally integrated apparatus including a magnetic resonance imaging scanner configured to record, from an examination region, MRT image data of a person under examination, a positron emission tomography scanner configured to record, from the examination region, PET image data of the person under examination, an additional scanning unit, and a single patient table, the method comprising:
   scanning, by the magnetic resonance imaging scanner and the positron emission tomography scanner, the examination region of the person under examination;
   scanning, by the additional scanning unit, an area of the person under examination;
   a contour of the person under examination in the scanned area based on the scanning;
   determining a location of structures that attenuate a PET signal based on the determined contour and the MRT image data; and
   carrying out an absorption correction of the recorded PET image data based on the determined location of the structures.

17. The method as claimed in claim 16, wherein the scanning is undertaken slice-by-slice.

18. The method as claimed in claim 16, wherein the scanning of the person under examination is undertaken by moving the patient table, on which the person under examination is arranged, through a scanning region of the additional scanning unit and by slice-by-slice scanning of the scanning region via the additional scanning unit.

19. The method as claimed in claim 16, wherein, during the scanning of the person under examination by way of the additional scanning unit, the scanning by the positron emission tomography scanner is carried out at the same time.

20. The method as claimed in claim 16, further comprising:
creating, based on the determined contour, an attenuation correction map of the scanned area, the attenuation correction map being used for the absorption correction of the PET data.

21. The method as claimed in claim 20, further comprising assigning areas lying within the determined contour a constant attenuation coefficient.

22. The method as claimed in claim 20, wherein the attenuation correction map is created taking into account information from the MRT image data recorded by way of the magnetic resonance imaging scanner.

23. The method as claimed in claim 16, wherein the additional scanning unit comprises a terahertz scanner configured to detect terahertz radiation emitted by the body of the person under examination or reflected on the body.

24. The method as claimed in claim 16, wherein the terahertz scanner is configured to detect the contour of the person under examination in a scanning region by emitting electromagnetic terahertz radiation and detecting terahertz radiation reflected at the person under examination.

25. The method as claimed in claim 16, wherein, during the scanning of the person under examination via the additional scanning unit, the scanning by the magnetic resonance imaging scanner is carried out at the same time.

26. The method as claimed in claim 16, wherein the scanning by the additional scanning unit scans a surface of a slice of the person under examination.

27. The method as claimed in claim 16, wherein the patient table and the additional scanning unit are movable relative to one another, and the scanning by the additional scanning unit scans the area of the person under examination slice-by-slice by relative movement between the patient table and the additional scanning unit.

28. The method as claimed in claim 27, wherein the patient table is configured to move the person under examination through the examination region such that the scanning by the additional scanning unit scans the area of the person under examination slice-by-slice upon moving the patient table.

29. The method as claimed in claim 16, wherein the additional scanning unit includes an x-ray scanner, designed to detect the contour of the person under examination in region examination region by emitting x-rays and detection of the x-rays scattered back from the person under examination.

30. The method as claimed in claim 16, wherein
the additional scanning unit has a larger field of view than the magnetic resonance imaging scanner and the positron emission tomography scanner.

* * * * *